United States Patent
Lowry et al.

(10) Patent No.: US 9,612,237 B2
(45) Date of Patent: Apr. 4, 2017

(54) RITALINIC ACID IMMUNOASSAY

(71) Applicant: Randox Laboratories Limited, Crumlin, Antrim (GB)

(72) Inventors: Philip Lowry, Crumlin (GB); Elouard Benchikh, Crumlin (GB); Ivan McConnell, Crumlin (GB); Peter Fitzgerald, Crumlin (GB)

(73) Assignee: Randox Laboratories Limited, Crumlin Antrim (GB)

( * ) Notice: Subject to any disclaimer, the term of this patent is extended or adjusted under 35 U.S.C. 154(b) by 374 days.

(21) Appl. No.: 14/186,650

(22) Filed: Feb. 21, 2014

(65) Prior Publication Data

US 2014/0242618 A1 Aug. 28, 2014

(30) Foreign Application Priority Data

Feb. 22, 2013 (GB) .................................. 1303158.8

(51) Int. Cl.
*G01N 33/53* (2006.01)
*C07K 16/44* (2006.01)

(52) U.S. Cl.
CPC ......... *G01N 33/5308* (2013.01); *C07K 16/44* (2013.01); *C07K 2317/33* (2013.01)

(58) Field of Classification Search
CPC . G01N 33/5308; C07K 16/44; C07K 2317/33
See application file for complete search history.

(56) References Cited

FOREIGN PATENT DOCUMENTS

WO 2009149252 A1 12/2009
WO 2011028875 A1 3/2011

OTHER PUBLICATIONS

Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Peterson et al., "Using hapten design to discover therapeutic monoclonal antibodies for treating methamphetamine abuse," J. Pharmacol. Exp. Ther., Jul. 2007; vol. 322, No. 1, pp. 30-39. Epub Apr. 23, 2007.*
Pravetoni et al., "Structurally distinct nicotine immunogens elicit antibodies with non-overlapping specificities," Biochem. Pharmacol., Feb. 15, 2012; vol. 83, No. 4, pp. 543-550, Published online Nov. 15, 2011.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Lewis, M.G., et al. An enzyme-linked immunosorbent assay (ELISA) for methylphenidate (Ritalin) in urine. J Anal Toxicol. Sep. 2003; 27(6):342-5.
Eichhorst, J., et al. Urinary screening for methylphenidate (Ritalin) abuse: a comparison of liquid chromatography-tandem mass spectrometry, gas chromatography-mass spectrometry, and immunoassay methods. Clin Biochem. Mar. 2004;37(3):175-83.
Search Report for priority application GB1303158.8 dated Aug. 13, 2013.

* cited by examiner

*Primary Examiner* — Galina Yakovleva
(74) *Attorney, Agent, or Firm* — Zackson Law LLC; Saul L. Zackson

(57) ABSTRACT

The invention provides novel antibodies which specifically bind to the methylphenidate metabolite, ritalinic acid, enabling an immunoassay that can detect methylphenidate in biological samples for an extended period following its ingestion. The invention also describes novel conjugates and kits incorporating the antibodies.

9 Claims, 4 Drawing Sheets

Methylphenidate

Ritalinic acid

RITALINIC ACID IMMUNOASSAY

CROSS-REFERENCE TO RELATED APPLICATIONS

This application claims the benefit of priority to UK Patent Application No. 1303158.8, filed on Feb. 22, 2013, which is incorporated herein by reference in its entirety.

DESCRIPTION

The invention relates to the field of immunodiagnostics and the detection of methylphenidate (MPH) use. MPH is a commonly prescribed drug used to treat depression, narcolepsy and attention deficit disorder. Due its amphetamine-like stimulant properties, it is subject to abuse and there have been numerous reports of its involvement in intoxication and overdose. As a drug of abuse, there is a clinical and forensic need to detect and quantify MPH in patient samples. In vivo, MPH is rapidly metabolised, thus analytical techniques used to detect MPH must be highly sensitive. Most analytical methods for MPH detection and quantification use the expensive, specialist operator-dependent technique liquid chromatography linked to mass-spectroscopy (LC-MS).

Immunodiagnostics is a relatively inexpensive and user-friendly analytical technology. There are numerous commercially available methylphenidate ELISA kits. However, immunoassays for MPH detection and quantification suffer from a limited detection window (the time-frame after MPH ingestion, during which MPH is detectable) due to MPH's rapid metabolism, undermining its use in forensic analysis. A study by Lewis et al (2003, Journal of Analytical Toxicology, 27:342-345) produced an ELISA for MPH detection in urine using a commercially available antibody stated, at page 343, right-hand column, to cross-react equally with MPH and the metabolite ritalinic acid (RA). The sheep antiserum to MPH was purchased from Cortex Biochem. The Lewis study states that their results are concordant with the commercially sourced Diagnostix assay. The Lewis study also states that the antibody was raised against ritalinic acid following conjugation to KLH (which the skilled person would interpret as conjugation via the carboxy group of RA) and, contradicting his earlier statement regarding concordance with the Diagnostix MPH-only assay, that it was equally specific for MPH and RA, MPH-thyroglobulin is immobilised onto the microtitre plate and competes with MPH in the sample for antibody binding sites. The skilled person is unable to interpret these conflicting statements and is unable to directly and unambiguously determine, from the Lewis study, the immunogen used to raise the Lewis antibodies—for example, the Abstract states 'sheep methylphenidate antibody'. The Abstract goes on to state that, after washing, sheep MPH antibody bound to the immobilised MPH is detected with peroxidase labelled goat anti-sheep IgG. The Lewis study also refers, in its introduction, to a commercially available ELISA (from Diagnostix Ltd. (Missisauga, ON, Canada) stated to detect both MPH and RA. Both assays are described as being susceptible to circumvention through urine dilution, that may be identified by creatinine correction. The circumvention through urine dilution is presumably due to the use of MPH-specific antibodies in the assay, in which the already low concentrations of MPH due to rapid metabolism are further reduced by dilution, thus producing a very low concentration of MPH for the MPH-specific antibodies to capture prior to detection. However, even with creatinine correction it would still be preferable to have an immunoassay which is ritalinic acid specific rather than methylphenidate specific. As the latter quickly metabolises to the former, ritalinic acid would be rapidly present in greater concentrations than methylphenidate meaning its detection would be less susceptible to be affected by dilution.

Abcam® produce a polyclonal sheep antibody to MPH. The Abcam antibody shows less than 0.9% cross-reactivity to RA. The Abcam antibody is raised using MPH-BTG as the immunogen.

A study by Eichhorst et al (2004, Clinical Biochemistry, 37:175-183) compared an ELISA purchased from Diagnostix Ltd. with LC/MS/MS and GCIMS. Page 176 states that the ELISA method produces an unacceptably high number of false-positives—approximately 10%. Even when a pre-extraction step was employed to remove potentially interfering substances, the false positive rate was only reduced to approximately 5%. Page 176, left hand column states that "ideally, any assay used for urinary MPH screening should be able to detect both parent and major metabolite" (MPH and RA, respectively). This study states (see page 179, right hand column concludes that the Diagnostix ELISA assay detects only parent MPH. The study concludes that LC/MS/MS "is far superior to the above-mentioned ELISA method and GC/PS" (see page 182, left hand column).

There remains a need for an antibody that is specific for ritalinic acid (RA).

SUMMARY OF THE INVENTION

The invention described herein, underpinned by a RA-specific antibody, overcomes the problems associated with MPH immunoassays. The highly specific RA antibody, which has negligible cross-reactivity to MPH, enables a sensitive assay with an extended detection window for the indirect detection of MPH use. The invention also describes methods, uses and substrates incorporating the RA-specific antibody.

DETAILED DESCRIPTION

Figure 1:
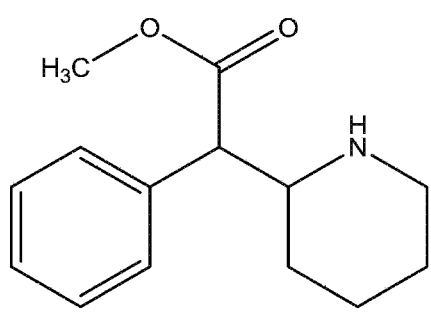
FIG. 1 illustrates structures of methylphenidate and ritalinic acid
Figure 1:
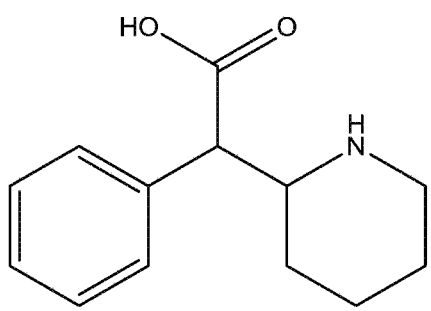

In a first aspect, the invention describes an antibody which binds specifically to an epitope of RA. When in used in reference to the antibody of the invention, the word 'specifically' implies that RA is almost exclusively bound by the antibody as gauged by a suitable metric such as the cross-reactivity. The analyte with the greatest cross-reactivity is given a value of 100%, with all other analytes accorded a value relative to this. In the present invention, the analyte, ritalinic acid, is given a value of 100%. As recognised by the skilled person, the antibody will also have a degree of binding to other molecules; the important aspect for the application of a practical RA-specific immunoassay is that the binding of the antibody to other molecules, especially structurally-related molecules such as MPH, is at such a relatively low level as to not compromise the assay's validity i.e. an assay with an extended detection window of MPH use. In this context, the cross-reactivity of the antibody to MPH is preferably less than 10%, more preferably less than 1.00%. Any suitable immunoglobulin-derived molecules (an 'antibody derivative') such as, but not limited to, a polyclonal, monoclonal, humanised, chimeric, short-chain or single chain variable fragments known to the skilled person can be used as the antibody in the immunoassay of the present invention. The antibody is preferably a polyclonal or a monoclonal antibody.

The RA epitope bound by the antibody of the invention preferably incorporates the hydroxyl group of RA. That the antibody of the invention is likely to bind the hydroxyl group of RA, and not the methoxy group of MPH, is supported by the cross-reactivity data (Table 1); MPH structurally differs from RA in that their carbonyl groups are covalently attached to a methoxy and hydroxyl group, respectively. This infers that the epitope bound by the antibody of the invention comprises the hydroxyl group of RA.

The standard technique of antibody production is immunisation of an animal with an immunogen. The immunogen for a small molecule generally comprises a hapten, optionally a crosslinker, and an antigenicity conferring carrier material such as a protein.

In a further embodiment, the antibody of the invention is preferably derived from, i.e. raised against, an immunogen that is derivatised through the meta or para positions of the aromatic ring of RA, preferably through the pare position (Structure I)

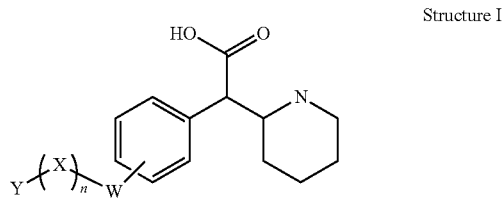

Structure I in which n is 0 or 1; W is NH, O or S: X is -Q-Z— in which Z is a crosslinking group selected from a $C_1$-$C_{10}$, preferably a $C_1$-$C_5$, substituted or unsubstituted straight or branched chain, saturated or unsaturated alkylene moiety and Q is, before conjugation to Y, a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof; Y is an antigenicity conferring carrier material which is preferably keyhole limpet haemocyanin (KLH), bovine thyroglobulin (BTG) or bovine serum albumin (BSA). Optionally, W is NH, n is 0, and Y is BSA.

In a second aspect, the invention describes a method of detecting or quantifying RA in an individual, the method comprising contacting an in vitro sample taken from the individual with a conjugate and an antibody of the invention, detecting the bound conjugate, and deducing from a calibrator value or calibrator values the presence or amount of RA. By detecting RA, the ingestion of MPH is highlighted. The conjugates of the method are made up of haptens attached to labelling agents. The haptens of the conjugates are molecules that can bind to the antibodies of the method. The use of haptens, conjugates and antibodies in the context of immunoassays is well known in the art. The labelling agent of the conjugates is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material. The individual's sample to be used for in vitro analysis can be any suitable biological tissue e.g. hair, but is preferably a biological fluid especially whole blood, serum, plasma or urine. Urine is the preferred fluid of analysis. The biological tissue or fluid may need preparation to render it suitable for analysis.

The antibody of the invention can be used in an immunoassay to detect or quantify the amount of RA in a liquid. The liquid can be a man-made solution or a biological fluid taken from an animal, preferably a mammal, most preferably from a human. If the liquid is a biological fluid taken from an animal, the detection of RA indicates that the animal has taken, been given or ingested MPH. Hence the immunoassay can be used to detect the use of MPH in animals, including *homo sapiens*. When referring to a RA immunoassay, although it is RA that is being detected, the preferable aim is to confirm intake of MPH. The detection or quantification of RA does not preclude the concomitant detection or quantification of MPH through a separate MPH-specific antibody. The detection and quantification criteria for an immunoassay platform includes, as is well-known in the art, exceeding a pre-defined cut-off/concentration value or measuring the calibrator equivalent value as derived from a calibrator curve (also referred to as a standard curve).

The format of an immunoassay for detecting or quantifying RA can be singleplex or multiplex; a singleplex immunoassay implies that only RA can be detected, while a multiplex immunoassay implies that RA is one of two or more analytes that can be detected. Generally, in a multiplex format, each analyte is detected by a different antibody specific to an individual analyte, although it may also be desirable to incorporate an antibody with generic binding properties i.e. an antibody that detects a number of similarly structured molecules.

The antibodies of the invention can be adsorbed on or covalently attached to a substrate. The substrate can be any medium or shape to which an antibody or antibody derivative can bind, either through chemical bonds (before which the substrate has to be chemically activated) or passive adsorption through mutual attraction of the substrate and antibody. Preferably, the antibodies are chemically bonded to the chemically activated substrate. The substrate can be for example plastic or magnetic beads, polystyrene microtitre plates (ELISA plates), planar nitrocellulose, a ceramic biochip of a biochip such as a plastic, glass or ceramic biochip surface-coated with a material that facilitates or optimises the functioning of the immunoassay. The antibodies or the substrate incorporating the antibodies can be provided as discrete off-the-shelf reagents.

In a third aspect is the invention describes a conjugate. The relevance of the conjugate to the method of invention is described previously. Preferably, the conjugate is of the following structure (Structure II)

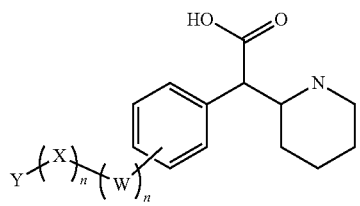

in which n=0 or 1 independently for each occurrence of n, with the proviso that n=1 for at least one of X or W; W, if present, is a functionalised group such as amino or carbonyl and is attached to the meta or pare position of the phenyl ring; X, if present, is a linking group capable of covalently bonding to Y and either W or the phenyl ring, which before introduction into Structure II can be cyanuric chloride or a functionalised $C_1$-$C_5$ alkyl chain: and Y is a detectable label such as HRP. The skilled person would recognise that when X is an alkyl chain it is required to be functionalised i.e. have reactive atoms/groups of atoms in order to bond to Y and W or phenyl. Optionally, n is 1 for W, W is NH, n is 0 for X, and is HRP. Preferably the conjugate is the 4-aminoritalinic acid-HRP conjugate of Example 6 of the Methods and Examples.

Without wishing to be bound by theory, it is proposed that it is possible to prepare an immunogen from 4-aminoritalinic acid (compound 4 in FIG. 2) as follows. The carboxy groups of BSA are activated (using e.g. succinic anhydride) following which the activated carboxy groups of BSA react with the amino group of the 4-aminoritalinic acid. In contrast, the free carboxylic acid group of 4-aminoritalinic acid is not activated and, therefore, does not react with BSA. The same principle applies for the preparation of a conjugate from 4-aminoritalinic acid. In this case, the carboxy groups of the HRP may be activated (using e.g. cyanuric chloride), which enables a conjugate to be formed.

In a fourth aspect the invention provides a kit comprising the antibodies of the invention, optionally attached or adsorbed to a substrate; optionally the kit has other components such as a conjugate of the invention and/or calibrators.

The unique properties of the RA-specific antibody also enables its use in RA detection and quantification for non-MPH related applications.

Enzyme Immunoassays, ELISAs

The enzyme-linked immunosorbent assay (ELISA) is a test that uses antibodies and colour change to identify a substance.

Antigens from the sample are attached to a surface. Then, a further specific antibody is applied over the surface so it can bind to the antigen. This antibody is linked to an enzyme, and, in the final step, a substance containing the enzymes substrate is added. The subsequent reaction produces a detectable signal, most commonly a colour change in the substrate.

Performing an ELISA involves at least one antibody with specificity for a particular antigen. The sample with an unknown amount of antigen is immobilized on a solid support (usually a polystyrene microtiler plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed to remove any proteins or antibodies that are not specifically bound. After the final wash step, the plate is developed by adding an enzymatic substrate to produce a visible signal, which indicates the quantity of antigen in the sample.

Lateral Flow Devices

In recent years, the in vitro diagnostics industry has made enormous efforts to develop immunochromatographic tests. Such tests have found applications in both clinical and non-clinical fields. A clinical utility of this test format is particularly suited to point of care utilities.

Rapid immunochromatographic test devices, e.g. in the form of a test strip, are made up of a number of components. Such a test strip commonly includes a sample pad, a conjugate pad, a membrane, e.g. a nitrocellulose membrane, and an absorbent pad. The membrane is usually attached by means of an adhesive to a supporting backing, e.g. made of plastic. In practice, the user dispenses a patient sample (such as urine or whole blood) onto the sample pad. The sample then flows through the sample pad into the conjugate pad, where it mixes with, and releases, the detector reagent. This mixture then flows across the membrane, where it binds with the test and control reagents located in the capture test zone (sample zone) and negative control zone, respectively. When the mixture binds to the reagent that forms the test line, a positive result is indicated. The colour intensity of the test line is proportional to the concentration of analyte in the sample. Excess sample that flows beyond the test and control zones is taken up in the absorbent pad.

Rapid immunochromatographic test devices for diagnostic purposes are easy to operate and thus do not only contribute to the comfort of professional users, e.g. medical stuff, but also allow the operation by non-professionals users, e.g. most patients.

Biochips

Biochips are components used for example in chemical analysis (including Proteomic and Molecular analysis) either to host a test reaction and/or to supply samples under test or reagents. Generally, a Biochip comprises a solid substrate, on which is arranged one or more test sites at which a reaction can take place in use. For instance, the test site may carry one or more reagents (e.g. ligands such as antibodies or antigens) adsorbed to the substrate, which are activated by the addition of a sample substance (e.g. analytes present in the sample bind to specific ligands). Such chips are sometimes referred to as a "lab on a chip" and can also incorporate tools for controlling steps of a reaction. As an example, one Biochip supplied by Randox Laboratories Limited (55 Diamond Road, Crumlin, County Antrim, United Kingdom, BT29 4QY) is used as a medium for performing multiplex analysis of biological samples using a chemiluminescence method. In this example, the Biochip takes the form of a small ceramic chip with a specialised surface preparation which is sensitive to environmental degradation. Therefore the Biochip is generally delivered in an environmentally sealed format, usually evacuated, sealed foil bags.

For instance, the Evidence™ analyser by Randox Laboratories Ltd uses biochips which are fitted into a plastic holder defining three recesses arranged in a line. Each recess is approximately square and sized to just accommodate a biochip, which is also square, with a small clearance to allow the chip to be placed. The "strip" of three mounted biochips is placed within a sealed foil bag for storage, which is then opened when the biochips are required for use. The plastic holder may be placed on a carrier alongside two further strips of three biochips to form a 3×3 array of biochips. The carrier has a keying feature for engagement with a robotic arm such that the array can be transported within the analyser via robotic handling. This configuration is useful for batch analysis.

A "Biochip" is a general term for a reaction platform for hosting chemical, biochemical, proteomic or molecular tests, as may be required for medical diagnosis, drug detection, etc. Typically, a Biochip comprises an inert substrate, such as silicon or glass (often of the order of about 1 $cm^2$ or less in surface area), on which one or a plurality of reaction sites is provided. The sites generally carry one or more ligands, for example, one or more antibodies, selected for the test (or "assay") to be performed, adsorbed to the surface of the chip for activation upon combination with a sample applied to the chip (e.g. a blood sample) and/or a reagent. The reactions can be detected using a number of alternative techniques, including detection of chemiluminescence generated by the reaction. Some biochips carry a very large number (hundreds or thousands) of such tests sites, typically arranged in a grid or array, making it possible to carry out numerous assays simultaneously, and using the same single specimen.

METHODS AND EXAMPLES

Preparation of Haptens, Immunogens and Detecting Agents

Although haptens provide defined structural epitopes, they are not in themselves immunogenic and therefore need to be conjugated to carrier materials, which will elicit an immunogenic response when administered to a host animal. As recognised by the skilled person, a hapten in the context of an immunoassay is a molecule (often less than 1000 daltons) that is to be conjugated to either a carrier material to form an immunogen or a detectable labelling agent to be used in a competitive immunoassay. Appropriate carrier materials commonly contain poly(amino acid) segments and include polypeptides, proteins and protein fragments. Illustrative examples of useful carrier materials are bovine serum albumin, egg ovalbumin, bovine gamma globulin, bovine thyroglobulin, keyhole limpet haemocyanin etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. As mentioned, the haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Immunogen formation for the invention described herein involves conventional conjugation chemistry. In order to confirm that adequate conjugation of hapten to earner material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount: of detecting agent bound to the antibodies which in turn is inversely proportionate to the analyte concentration. The signal can be detected or quantified by comparison with a calibrator.

Figure 2:
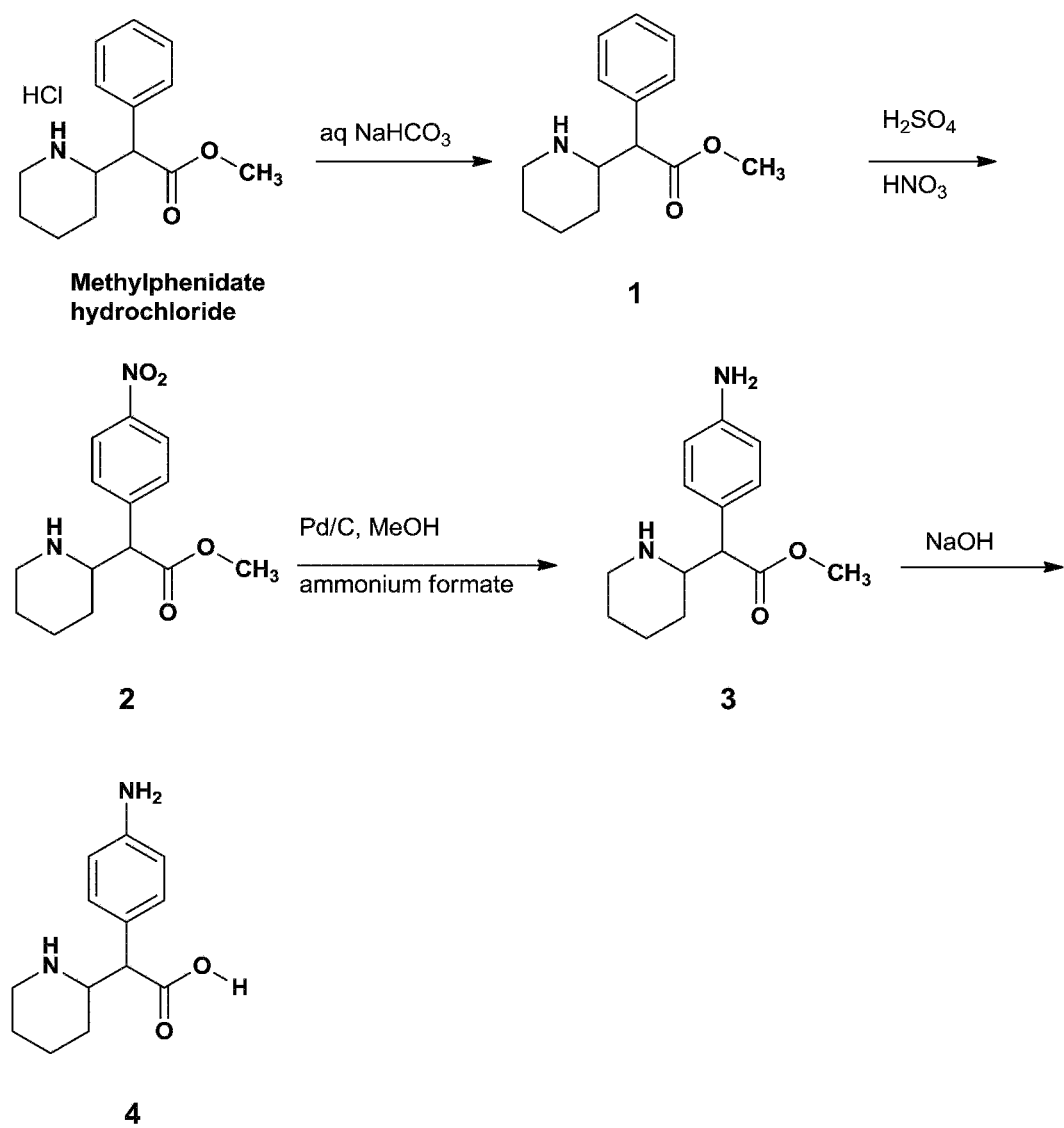
FIG. 2 illustrates synthesis of 2-(4-aminophenyl)-2-(piperidin-2-yl)acetic acid (i.e. 4-aminoritalinic acid)

Boldened numbers in the following Examples correspond to the numbers of FIG. 2.

Example 1

Preparation of Methylphenidate (Free Base) 1

Methylphenidate hydrochloride (2 g, 7.41 mmol) was dissolved in water (50 ml) and sodium bicarbonate was added until the pH was 9-10. The resulting mixture was stirred at room temperature for one hour. The reaction mixture was extracted several times with dichloromethane, the combined organic layers were washed with brine, dried over sodium sulfate and concentrated in vacuo to give methylphenidate free base 1 (1.7 g) as a light yellow oil.

Example 2

Preparation of methyl 2-(4-nitrophenyl)-2-(piperidin-2-yl) acetate 2

Fuming nitric acid (2 ml) was added portion-wise to an ice-cooled solution of methylphenidate free base 1 (1.7 g, 7.4 mmol) in concentrated sulfuric acid (10 ml) and the reaction mixture was stirred at room temperature for four hours. Fuming nitric acid (3 ml) was added and the resulting mixture was stirred for a further one hour at room temperature. The reaction mixture was cooled at 0° C. and sodium hydroxide 6N aqueous solution was added until alkaline. The aqueous solution was extracted with dichloromethane and the combined organic layers were washed with brine, dried over sodium sulfate and concentrated in vacuo to give a crude oil (2.062 g). The residue was purified by column chromatography (Biotage, 50 g SNAP cartridge, 0-5% methanol dichloromethane, two separations needed) to give methyl 2-(4-nitrophenyl)-2-(piperidin-2-yl) acetate 2 (1.29 g, 63% yield).

Example 3

Preparation of methyl 2-(4-aminophenyl)-2-(piperidin-2-yl) acetate 3

Methyl 2-(4-nitrophenyl)-2-(piperidin-2-yl) acetate 2 (1.29 g, 4.63 mmol) was dissolved in methanol (50 ml) and ammonium formate (1.58 g, 25 mmol) was added followed by addition of palladium on charcoal 5% (272 mg) at room temperature. The reaction mixture was stirred for one hour at room temperature and further palladium on charcoal 5% (272 mg) was added. The reaction mixture was stirred for one hour at room temperature then filtered Celite™, washed with methanol and the solvent was evaporated to give a crude oil (1.449). The residue was purified by column chromatography (silica gel, 10% Methanol in dichloromethane) to give 919 mg (81% yield) methyl 2-(4-aminophenyl)-2-(piperidin-2-yl) acetate 3.

Example 4

Preparation of 2-(4-aminophenyl)-2-(piperidin-2-yl) acetic acid 4 (4-amino RA)

Methyl 2-(4-aminophenyl)-2-(piperidin-2-yl) acetate 3 (0.91 g, 3.75 mmol) was dissolved in water (3.33 ml) and a solution of sodium hydroxide (6M) (1.667 ml, 9.38 mmol) was added. The reaction mixture was stirred at room temperature for two hours. The pH was adjusted to three using HCL 6N aqueous solution, the solvent removed in vacuo, the residue dissolved in methanol and charcoal added. The resulting solution was filtered on a silica plug to give (quantitative yield) of 2-(4-aminophenyl)-2-(piperidin-2-yl) acetic acid (912 mg) 4 as a viscous brown oil that solidified upon cooling.

Example 5

Immunogen formation: conjugation of 2-(4-aminophenyl)-2-(piperidin-2-yl) acetic add 4 to BSA To a solution of BSA (200 mg) in sodium bicarbonate (0.1M) solution pH 9.5 (10 mL) was added succinic anhydride (120 mg) in DMF (1 mL) while stirring and the resulting solution stirred at room temperature for four hours. Excess succinic anhydride was removed by dialysis against PBS pH 7.22. N-hydroxysuccinimide (96 mg) and EDC.HCl (160 mg) was added to succinated BSA solution and the mixture stirred at RT (room temperature) for two hours. 2-(4-Aminophenyl)-2-(piperidin-2-yl) acetic acid 4 (120 mg) in DMF (1.0 ml) was added to the activated succinated BSA and the mixture was stirred at room temperature overnight. The solution was dialysed against 50 mM phosphate buffer pH 7.2 (three changes) for 24 hours at 4° C. and freeze-dried to give the immunogen.

MALDI results showed that 18.02 molecules 4-aminoritalinic acid 4 had been conjugated to one molecule of succinated BSA.

Example 6

Conjugate formation: conjugation of 2-(4-aminophenyl)-2-(piperidin-2-yl) acetic acid 4 (4-aminoritalinic acid) to HRP To a solution of HRP (20 mg) in carbonate buffer (50 mM), pH 9.4 (0.8 mL) was added cyanuric chloride (2 mg) and the mixture was stirred at room temperature for two and a half hours. Excess was removed by dialysis at 4° C. against carbonate buffer (50 mM), pH 9.4 in the dark. 4-Aminoritalinic acid 4 (5 mg) DMF (0.5 mL) was added to cyanuric chloride activated HRP and the mixture was incubated on a shaker set at 200 rpm at 37° C. overnight in the dark. Excess hapten was removed with PD-10 column (Pharmacia), pre-equilibrated with phosphate-buffered saline, pH 7.2 followed by dialysis at 4° C. against phosphate-buffered saline, pH 7.2.

Figure 4:
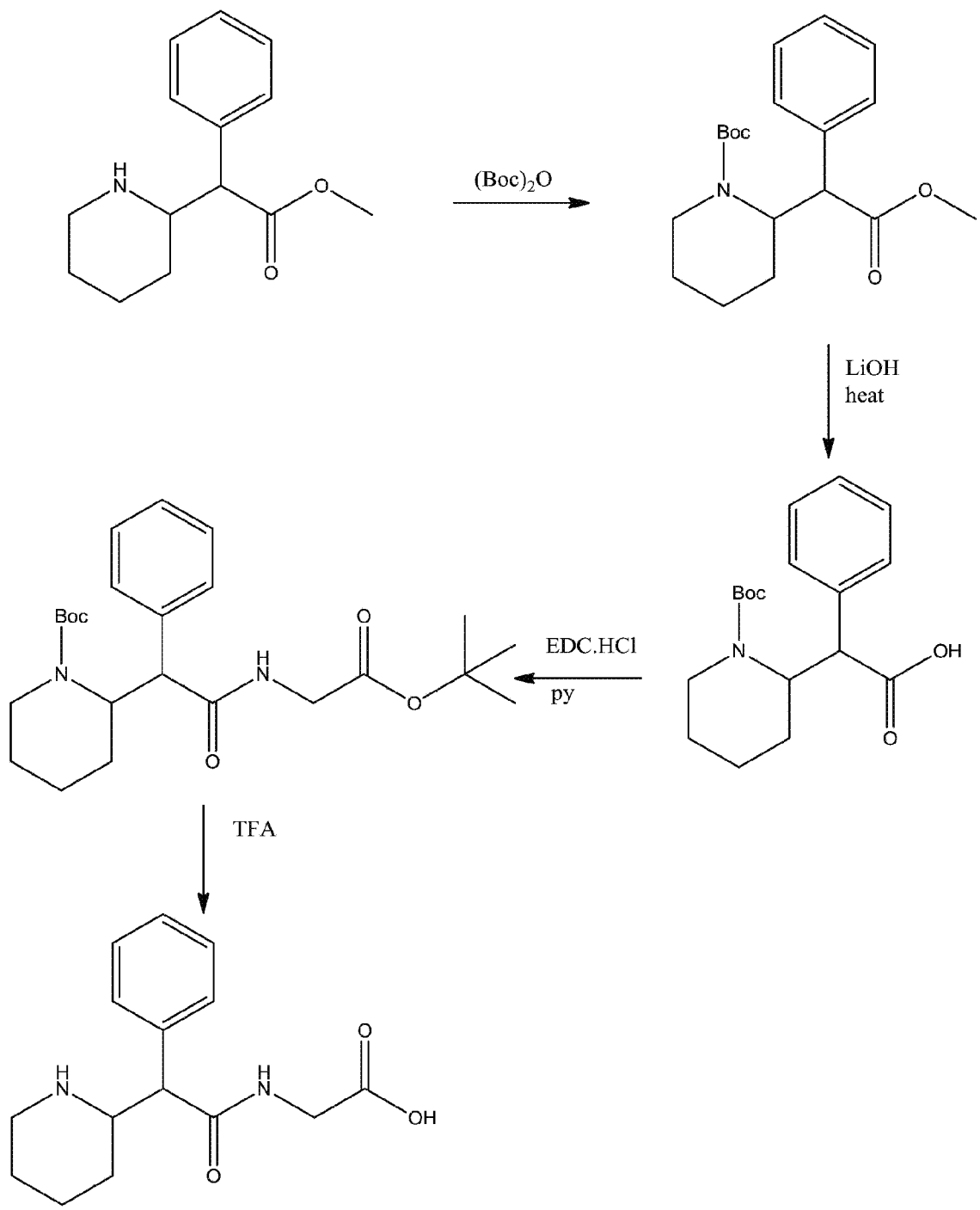
FIG. 4 illustrates alternative synthesis of 2-(2-phenyl-2-(piperidin-2-yl)acetamido)acetic acid trifluoroacetate salt

For following Examples 7-10, reference is made to FIG. 4.

Comparative Example 7

Synthesis of N-Boc-Methylphenidate

A mixture of methylphenidate hydrochloride (974 mg, 3.61 mmol), di-tert-butyldicarbonate (945 mg, 4.33 mmol) and triethylamine (1.51 ml, 10.83 mmol) in dichloromethane (30 ml) was stirred at RT overnight. Solvents were removed in vacuo and crude purified by column chromatography (silica gel:ethyl acetate) to give the title compound (1.32 g) as a slightly crude oil which solidified on standing.

Comparative Example 8

N-Boc-Ritalinic Acid

N-Boc methylphenidate (1.32 g) was dissolved in methanol (30 ml). 1 M lithium hydroxide solution was added to attain pH 14. The mixture was heated at 60° C. for 48 h. The mixture was neutralised to pH 7 using 1M sulphuric acid and methanol removed in vacuo. A precipitate resulted which was recovered by vacuum filtration with water wash. The product obtained was dried in a dessicator over phosphorous pentoxide, overnight. This gave the title compound (890 mg) as a white solid.

Comparative Example 9

N-Boc-(2-(2-phenyl-2-(piperidin-2-yl)acetamido) acetic acid t-butyl ester)

N-Boc-ritalinic acid (885 mg, 2.7 mmol) was dissolved in pyridine (20 ml). To this was added EDC.HCl (797 mg, 4.05 mmol) and glycine t-butyl ester (697 mg, 4.05 mmol). The mixture was stirred at RT overnight. Solvents were removed in vacuo and the crude was purified by column chromatography (silica gel: 50% ethyl acetate in hexane) to give the title compound (685 mg, 57%) as a white solid.

Comparative Example 10

2-(2-phenyl-2-(piperidin-2-yl)acetamido)acetic acid Trifluoroacetate salt

N-Boc-(2-(2-phenyl-2-(piperidin-2-yl)acetamido)acetic acid t-butyl ester) (670 mg, 1.55 mg) was dissolved in dichloromethane (10 ml). Trifluoroacetic acid (10 ml) was added and mixture stirred at RT overnight. The reaction was evaporated to dryness and the crude residue was triturated with diethyl ether (2×50 ml). This gave the title compound (526 mg, 87%) as a tan solid.

Analysis: ES-MS. Expected M+1=277.1552. Obtained M+1=277.1535

Comparative Example 11

Immunogen Formation: Conjugation of 2-(2-phenyl-2-(piperidin-2-yl)acetamido)acetic acid Trifluoroacetate Salt to BTG The methodology used to generate the title immunogen was standard methodology, for example as described in Comparative Example 14 with appropriate adaptation, as would be appreciated by the skilled person.

Comparative Example 12

Conjugate Formation: Conjugation of 2-(2-phenyl-2-(piperidin-2-yl)acetamido)acetic acid Trifluoroacetate Salt to HRP EDC hydrochloride (10 mg) was dissolved in water (0.5 ml) and immediately added to a solution of 2-[2-phenyl-2-(piperidin-2-yl)acetamido]acetic acid trifluoroacetate salt (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The HRP conjugate was then dialysed overnight against 10 L of PBS at pH 7.2 at 4° C.

Comparative Example 13

Immunogen Formation: Conjugation of RA to BSA

To a solution of RA (16.7 mg, 0.076 mmol) in DMF (1.0 ml) was added N, N-dicyclohexylcarbodiimide (DCC) (17.06 mg, 0.082 mmol) and N-hydroxysuccinimide (9.52 mg, 0.082 mmol) and the mixture was stirred at room temperature overnight. The dicyclohexylurea formed was removed by filtration and the solution was added drop-wise to a solution of BSA (100 mg, 1.5 µmol) in 50 mM sodium bicarbonate solution (pH 8.5) (5 ml). The mixture was then stirred overnight at 4° C. The solution was then dialysed against 50 mM phosphate buffer pH 7.2 (3 changes) for 24 hours at 4° C. and freeze-dried. MALDI results showed 8.7 molecules of RA had been conjugated to one molecule of BSA.

Comparative Example 14

Immunogen Formation: Conjugation of RA to BTG

To a solution of RA (29.6 mg, 0.135 mmol) DMF (1.0 ml) was added N,N-dicyclohexylcarbodiimide (DCC) (31.0 mg, 0.149 mmol) and N-hydroxysuccinimide (17.13 mg, 0.149 mmol) and the mixture was stirred at room temperature overnight. The dicyclohexylurea formed was removed by filtration and the solution was added dropwise to a solution of BTG (150 mg) in 50 mM sodium bicarbonate solution (pH 8.5) (10 ml). The mixture was then stirred overnight at 4° C. The solution was then dialysed against 50 mM phosphate buffer (pH 7.2) (3 changes) for 24 hours at 4° C., and freeze-dried.

Example 15

Antibody Production

Immunogen (2 mg) from Examples 5 or 11 was prepared in PBS, mixed at a ratio of 50% immunogen in PBS to 50% Freund's Complete Adjuvant (Sigma, Product Number F5881) and emulsified by repeatedly passing the mixture through a tip on the end of a 1 ml syringe, until semi-solid. The emulsified mixture (1 ml) was injected intramuscularly into the sheep (the primary immunisation dose). Further injections (boosts) were prepared (1 mg of immunogen is prepared in PBS and mixed at a ratio of 50% immunogen PBS/50% Freunds Incomplete adjuvant, Sigma, Product Number—F5506) and injected (1 ml) intramuscularly at monthly intervals. Serum was sampled monthly by collection of whole blood from the jugular vein for evaluation of the antibody titre. Prior to immobilisation on a solid substrate (for example, the biochip), the serum was purified using caprylic acid/ammonium sulphate precipitation, as described for example in Chapter 4 of "Making and Using Antibodies—A Practical Handbook" $2^{nd}$ Edition, edited by G C Howard and M R Kaser, CRC Press.

Example 16

Generation of Standard Curves Using Generated Antiserum Raised Against the Immunogen of Example 5 (BioChip Solid Substrate Platform)

The HRP depleted IgG fraction of the antiserum raised against the immunogen (immunogen of Example 5) was immobilized to the surface of the Randox Biochip in a discrete test region (see EP0874242, incorporated herein by reference in its entirety). The HRP depletion was carried out prior to IgG immobilization, in order to remove any HRP-substrates from the IgG fraction, thereby preventing IgG-derived non-specific interactions to HRP once immobilized on the Biochip. HRP depletion was achieved by passing the IgG fraction through a column incorporating HRP coupled to resin. The flow-through represents the HRP-depleted IgG fraction used on the Biochip.

A competitive chemiluminescent immunoassay was employed for the assay with the drug in the specimen and drug labelled with horseradish peroxidase (2-(4-aminophenyl)-2-(piperidin-2-yl) acetic acid conjugated to HRP—Example 6) being in direct competition for the antibody binding site. Increased levels of drug will lead to reduced binding of drug labelled with HRP and thus a reduction in the chemiluminescent signal emitted. The light signal generated from the test regions on the biochip was detected using digital imaging technology and compared to that from a calibration curve. The concentration of analyte present is calculated from the calibration curve. RA was prepared in buffer base at 500 ng/ml and serially diluted 2-fold to give 8 additional levels of 250 ng/ml, 125 ng/ml, 62.5 ng/ml, 31.25 ng/ml, 15.63 ng/ml, 7.81 ng/ml, 3.91 ng/ml and a blank at 0 ng/ml (Similarly for Methylphenidate at levels of 78.125 ng/ml, 156.25 ng/ml, 312.50 ng/ml, 625 ng/ml, 1,250 ng/ml, 2,500 ng/ml, 5,000 ng/ml, 10,000 ng/ml) 0.25 µl of each standard was added to each well of the 9 well Biochip carrier with 155 µl of BSA-containing assay diluent. Drug labelled horseradish peroxidase (120 µl) was then added to each well and incubated for 30 min at 30° C. at 370 rpm using a Randox Investigator thermoshaker. Following incubation, the liquid was decanted and the wells were washed with Evidence wash buffer, 6 quick washes and 6 two minute soaks were completed after which the liquid was decanted and the carrier tapped onto lint free paper. Luminol-EV841 & Peroxide were mixed (1:1) to give working strength signal reagent and 250 µl added to each well. The Biochip carrier was then incubated for 2 minutes protected from light and imaged using the Evidence Investigator camera. The Relative Light Units (RLU) produced are shown in Table 1 at each concentration of RA and MPH tested.

Results

TABLE 1

Data generated from biochip assay for RA and methylphenidate employing antibodies of the invention (antisera generated in response to immunogen of Example 5) and (2-(4-aminophenyl)-2-(piperidin-2-yl) acetic acid conjugated to HRP (Example 6)

| RA | | | Methylphenidate | | |
|---|---|---|---|---|---|
| Calibrator conc$^n$ (ng/ml) | RLU | B/B$_0$ % | Calibrator conc$^n$ (ng/ml) | RLU | B/B$_0$ % |
| 0.00 | 6321 | 100 | 0.00 | 4437 | 100 |
| 3.91 | 3459 | 65 | 78.13 | 3878 | 87 |
| 7.81 | 2552 | 40 | 156.25 | 3604 | 81 |
| 15.63 | 1980 | 31 | 312.50 | 3319 | 75 |
| 31.25 | 1111 | 18 | 625 | 2912 | 66 |
| 62.50 | 677 | 11 | 1,250.00 | 2244 | 51 |
| 125.00 | 374 | 6 | 2,500.00 | 1517 | 34 |
| 250.00 | 247 | 4 | 5,000.00 | 1015 | 23 |
| 500.00 | 134 | 2 | 10,000.00 | 697 | 16 |
| Cross-reactivity 100% | | | Cross-reactivity 0.4% | | |
| IC$_{50}$ = 5.21 ng/ml, | | | IC$_{50}$ = 1,323.50 ng/ml | | |
| LOD = 0.50 ng/ml | | | | | |

RLU=relative light units; B=RLU at xng/ml calibrator concentration; B$_0$=RLU at 0 ng/ml calibrator concentration; IC$_{50}$=calibrator concentration which produces 50% B/B$_0$; % CR=percentage cross-reactivity based on 100% specificity to RA; LOD=limit of detection.

TABLE 2

Drugs exhibiting no cross-reactivity at given concentration

| Compound | No measurable CR at given concentration |
|---|---|
| Ethylphenidate | 100 µg/ml |
| mCPP | 10 µg/ml |
| fluoxetine | 100 µg/ml |
| Tramadol | 10 µg/ml |
| Haloperidol | 10 µg/ml |
| Acetoaminophen | 1000 µg/ml |
| Ibuprofen | 1000 µg/ml |
| N-desmethylescitalopram | 10 µg/ml |
| Norsertraline | 10 µg/ml |
| Ethyl glucuronide | 100 µg/ml |
| Salicylic acid | 1000 µg/ml |
| Dextromorphan | 10 µg/ml |
| Nortriptylene | 10 µg/ml |

Tables 1 and 2 confirm the specificity of the antibodies of the invention for RA enabling the extended detection of methylphenidate use by individuals.

Example 17

Generation of Standard Curves Using Generated Antiserum Raised Against the Immunogen of Example 5 (ELISA Platform)

The ELISA data provided below correspond to the same immunogen, antibody and tracer combination used to generate the Biochip standard curves, i.e. antibodies of the invention (antisera generated in response to immunogen of Example 5) and (2-(4-aminophenyl)-2-(piperidin-2-yl) acetic acid conjugated to HRP (Example 6). The assay methodology used to generate the ELISA data was standard ELISA methodology. Briefly, a microtitre plate was coated with Ig fraction of the antiserum produced at 5 µg/ml, prepared in Tris buffer, pH8.5. The coated plate was simultaneously incubated with calibrator/sample (from 0 ng/ml-80 ng/ml) and HRP conjugate at ⅛K dilution. After washing and substrate addition, absorbances were read at 450 nm. The absorbance in each well was inversely proportional to the concentration of ritalinic acid or methylphenidate hydrochloride in the calibrator/sample added to that well.

Results

TABLE 3

Data generated from ELISA for RA and methylphenidate employing antibodies of the invention (antisera generated in response to immunogen of Example 5 and 2-(4-arninophenyl)-2-(piperidin-2-yl) acetic acid conjugated to HRP (Example 6)

| Conc. ng/ml | Ritalinic Acid (LK839) | | | Methylphenidate Hydrochloride | | |
|---|---|---|---|---|---|---|
| | Ave OD | % CV | B/Bo | Ave OD | % CV | B/Bo |
| 0 | 1.634 | 1.3 | 100.0 | 1.645 | 2.0 | 100.0 |
| 1.25 | 1.346 | 2.6 | 82.4 | 1.677 | 2.8 | 101.9 |
| 2.5 | 1.169 | 1.3 | 71.5 | 1.644 | 1.4 | 99.9 |
| 5 | 0.987 | 0.8 | 60.4 | 1.635 | 1.0 | 99.4 |
| 10 | 0.751 | 2.5 | 46.0 | 1.563 | 1.3 | 95.0 |
| 20 | 0.584 | 4.7 | 35.7 | 1.476 | 1.0 | 89.7 |
| 40 | 0.424 | 1.6 | 26.0 | 1.402 | 1.6 | 85.2 |
| 80 | 0.311 | 2.9 | 19.0 | 1.311 | 7.7 | 79.7 |
| IC$_{50}$ | 8.41 ng/ml | | | >>>80 ng/ml | | |
| % CR | 100 | | | <<<10.5 | | |

Comparative Example 18

Generation of Standard Curves Using Generated Antiserum Raised Against the Immunogen of Example 11 (2-(2-phenyl-2-piperidin-2-yl)acetamido)acetic acid trifluoroacetate Salt Conjugated BTG) (BioChip Solid Substrate Platform)

A competitive chemiluminescent immunoassay was employed for the assay with the drug in the specimen and drug labelled with horseradish peroxidase (2-(2-phenyl-2-(piperidin-2-yl)acetamido)acetic acid Trifluoroacetate salt conjugated to HRP—Example 12) being in direct competition for the antibody binding site. Increased levels of drug will lead to reduced binding of drug labelled with HRP and thus a reduction in the chemiluminescent signal emitted. The assay methodology was as per Example 16 above.

Results

TABLE 4

Drugs exhibiting no cross-reactivity at given concentration

| Compound | Concentration |
|---|---|
| acetaminophen | 2.5 mg/ml |
| 4-acetamidophenyl β-D-glucuronide sodium salt | 250 µg/ml |
| 4-acetaminophen sulphate potassium salt | 250 µg/ml |
| 4-aminosalicylic acid | 250 µg/ml |
| aspirin | 250 µg/ml |
| benorylate HCl | 250 µg/ml |
| benzoic acid | 250 µg/ml |
| 1-benzylpiperiazine | 10 µg/ml |
| buprenorphine | 10 µg/ml |
| BZG | 10 µg/ml |
| citalopram hydrobromide salt | 7.5 µg/ml |
| codeine | 250 ng/ml |
| (−)-cotinine | 22 µg/ml |
| 3-cysteinylacetaminophen trifluoroacetic acid salt | 250 µg/ml |
| delta-9-THC | 10 µg/ml |

TABLE 4-continued

Drugs exhibiting no cross-reactivity at given concentration

| Compound | Concentration |
|---|---|
| dextromethorphan hydrobromide monohydrate | 10 µg/ml |
| dextrorphan tartrate salt | 250 ng/ml |
| D-amphetamine | 10 µg/ml |
| D-glucuronic acid | 60 µg/ml |
| diazepam | 3 µg/ml |
| diflusinal | 250 µg/ml |
| 2,3-dihydroxy benzoic acid | 250 µg/ml |
| ethyl-β-D-glucuronide | 100 µg/ml |
| etoperidone HCl | 400 ng/ml |
| fentanyl | 10 µg/ml |
| fluoxetine HCl | 10 µg/ml |
| gentisic acid | 250 µg/ml |
| gentisuric acid | 250 µg/ml |
| haloperidol | 10 µg/ml |
| heroin | 10 µg/ml |
| hydrocodone | 10 µg/ml |
| hydromorphone | 10 µg/ml |
| 1-(3-hydroxyphenyl)-piperazine | 400 ng/ml |
| ibufenac | 250 µg/ml |
| ibuprofen | 1 mg/ml |
| ibuprofen carboxylic acid | 250 µg/ml |
| ketoprofen | 250 µg/ml |
| levorphanol | 250 ng/ml |
| lorazepam | 3 µg/ml |
| LSD | 10 µg/ml |
| MAMP | 2.5 µg/ml |
| MDEA | 2.5 µg/ml |
| MDMA | 5 µg/ml |
| mebutamate | 350 ng/ml |
| meprobamate | 10 µg/ml |
| methacetin | 250 µg/ml |
| methadone | 10 µg/ml |
| methaqualone | 10 µg/ml |
| methyl salicylate | 250 µg/ml |
| 3-methoxymorphinan HCl | 250 µg/ml |
| morphine sulphate | 10 µg/ml |
| N-acetylbenzoquinomeimine | 125 µg/ml |
| naproxen | 250 µg/ml |
| 3-(N-acetyl-L-cystein-s-yl) acetaminophen sodium salt | 250 µg/ml |
| N-desmethyl dextorphan | 250 ng/ml |
| N-desmethyl escitalopram hydrobromide | 10 µg/ml |
| N-desmethyl sertraline HCl | 10 µg/ml |
| 7-NH flunitrazepam | 10 µg/ml |
| (−)-nicotine | 22 µg/ml |
| nordiazepam | 3 µg/ml |
| normeperidine | 1 µg/ml |
| (+)-norpropoxyphene maleate | 10 µg/ml |
| nortriptyline HCl | 10 µg/ml |
| oxazepam | 3 µg/ml |
| oxycodone | 10 µg/ml |
| phenacetin | 250 µg/ml |
| phenobarbital | 10 µg/ml |
| p-phenetidine | 106.35 µg/ml |
| phenethylamine sulfate | 250 µg/ml |
| p-trifluoromethylphenol | 2.5 µg/ml |
| rac-2-hydroxy ibuprofen | 125 µg/ml |
| rac N-bisdesmethyl tramadol HCl | 180 ng/ml |
| rac N,O-didesmethyl tramadol | 180 ng/ml |
| (R)-citalopram oxalate | 1500 ng/ml |
| (R)-(−)-ibuprofen | 250 µg/ml |
| S-(+)-ibuprofen | 250 µg/ml |
| salicylic acid B-D glucuronide | 125 µg/ml |
| salicylic acid | 1 mg/ml |
| salicyluric acid | 250 µg/ml |
| salsalate | 250 µg/ml |
| sertraline | 7.5 µg/ml |
| sertraline carbamoyl glocuronide | 3 µg/ml |
| temazepam | 3 µg/ml |
| tramadol HCl | 10 µg/ml |
| trazodone HCl | 10 µg/ml |
| trazodone N-oxide | 400 ng/ml |
| trichloroacetic acid | 100 µg/ml |
| urochloralic acid | 100 µg/ml |
| venlafaxine HCl | 180 ng/ml |
| zaleplon | 10 µg/ml |
| zopiclone | 10 µg/ml |
| zolpidem tartrate | 10 µg/ml |

TABLE 5

Data generated from biochip assay for compounds including RA and methylphenidate employing antisera generated in response to immunogen of Example 11 and conjugate of Example 12

| Compound | % cross reactivity |
|---|---|
| methylphenidate HCl | 100 |
| rac-erythro-ethylphenidate HCl | 1.9 |
| ritalinic acid | 1.0 |
| (+)-pseudoephedrine HCl | 0.2 |
| flurazepam | <1 |
| PCP | <0.1 |

Figure 3:
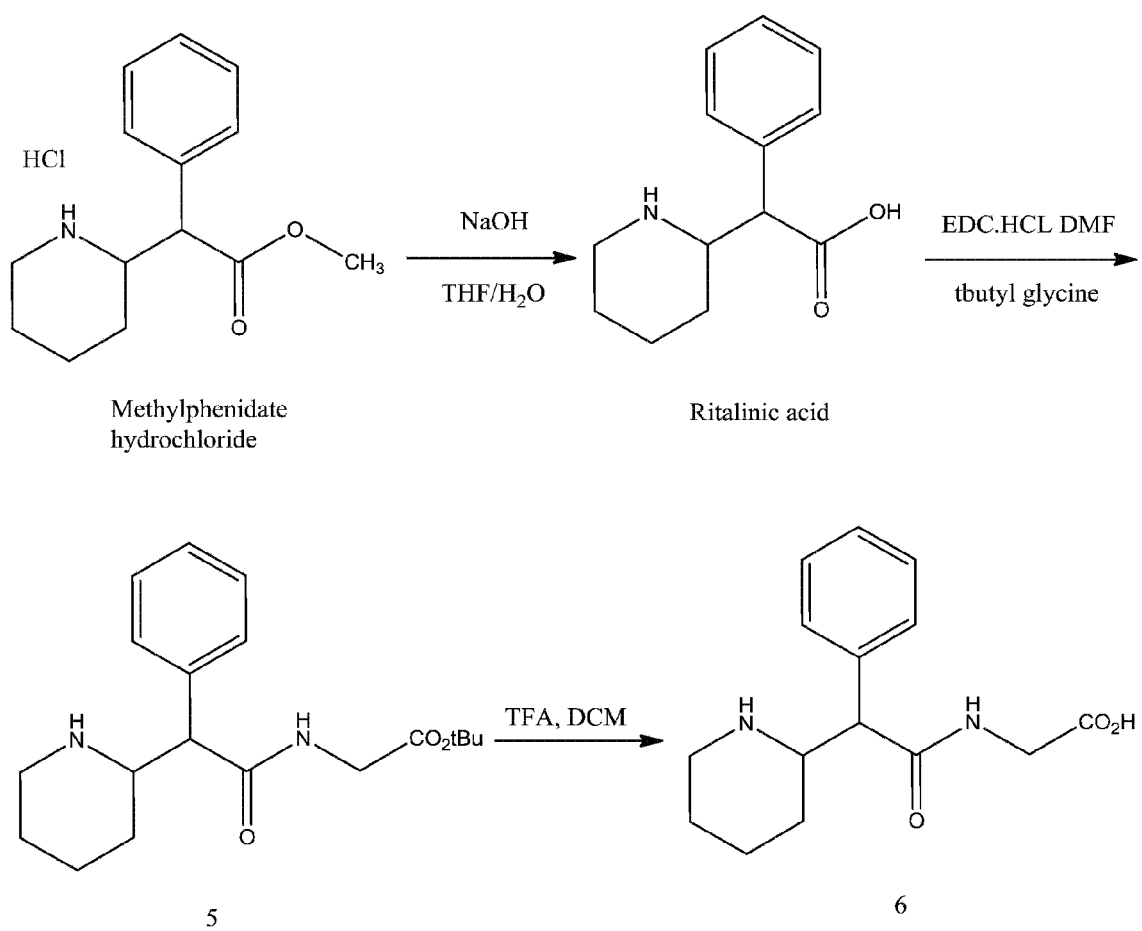
FIG. 3 illustrates synthesis of 2-(2-phenyl-2-(piperidin-2-yl)acetamido)acetic acid trifluoroacetate salt

These comparative data show that antibodies raised to the immunogen 2-[2-phenyl-2-(piperidin-2-yl)acetamido]acetic acid trifluoroacetate salt (shown as the final compound in FIG. 4, also as compound 6 of FIG. 3) conjugated to BTG (Example 11), were specific to methylphenidate ($IC_{50}$=2.6 ng/ml, cross-reactivity=100%) and showed minimal binding to RA ($IC_{50}$=260 ng/ml cross-reactivity=1%).

What is claimed is:

1. An antibody which binds specifically to ritalinic acid, wherein the antibody has less than 1% cross-reactivity to methylphenidate relative to 100% cross-reactivity to ritalinic acid using (2-(4-aminophenyl)-2-(piperidin-2-yl) acetic acid-horse radish peroxidase as a tracer.

2. The antibody of claim 1, wherein the antibody is raised against 2-(4-aminophenyl)-2-(piperidin-2-yl) acetic acid conjugated to bovine serum albumin.

3. The antibody of claim 1, wherein the antibody is a polyclonal antibody.

4. A solid substrate upon which the antibody of claim 1 is immobilized.

5. The solid substrate of claim 4 wherein the substrate is selected from the group consisting of a biochip and a microtitre plate.

6. A method of detecting or quantifying ritalinic acid in an individual, the method comprising:
providing an in vitro sample from an individual; and
detecting ritalinic acid if present in the sample by contacting the sample with the antibody of claim 1 and detecting binding between the ritalinic acid and the antibody.

7. A method of detecting or quantifying ritalinic acid in an individual in accordance with claim 6, wherein the detecting binding comprises performing a competitive chemiluminescent immunoassay and deducing from a calibrator value or calibrator values the presence or amount of ritalinic acid.

8. The method of claim 6 wherein the in vitro sample is a urine sample.

9. A kit comprising an antibody according to claim 1.

* * * * *